United States Patent
Kubena et al.

(10) Patent No.: US 8,323,351 B2
(45) Date of Patent: Dec. 4, 2012

(54) SELF-EXPANDING PLASTIC STENT

(75) Inventors: Petr Kubena, Hradec Kralove (CZ); Lucie Kotalova, Hradec Kralove (CZ)

(73) Assignee: Ella-CS, S.R.O., Hradec Kralove (CZ)

( * ) Notice: Subject to any disclaimer, the term of this patent is extended or adjusted under 35 U.S.C. 154(b) by 152 days.

(21) Appl. No.: 12/901,418

(22) Filed: Oct. 8, 2010

(65) Prior Publication Data

US 2011/0087336 A1 Apr. 14, 2011

(51) Int. Cl.
*A61F 2/04* (2006.01)
(52) U.S. Cl. ............... 623/23.7; 623/1.51; 623/1.53
(58) Field of Classification Search .......... 623/1.53, 623/23.7, 1.15, 1.49, 1.51
See application file for complete search history.

(56) References Cited

U.S. PATENT DOCUMENTS

| | | | |
|---|---|---|---|
| 2001/0056299 A1 | 12/2001 | Thompson | |
| 2002/0098278 A1* | 7/2002 | Bates et al. | 427/2.1 |
| 2004/0039441 A1* | 2/2004 | Rowland et al. | 623/1.42 |
| 2008/0319247 A1* | 12/2008 | Forbes et al. | 600/9 |
| 2009/0157158 A1 | 6/2009 | Ondracek et al. | |
| 2009/0275974 A1 | 11/2009 | Marchand et al. | |

FOREIGN PATENT DOCUMENTS

WO WO 01/56505 8/2001

OTHER PUBLICATIONS

LeMoine et al., :Self-expanding plastic stents for benign esophageal lesions, Gastrointest. Endosc. 60(6):894-900 (Drc. 2004) (Abstract only).
Zeus Whitepaper, "PEEK vs. Metal: Why Plastic is Better", Zeus Industrial Products, Inc., Copyright 2005.

* cited by examiner

*Primary Examiner* — Thomas J Sweet
*Assistant Examiner* — Matthew Schall
(74) *Attorney, Agent, or Firm* — Richard C. Litman

(57) ABSTRACT

The self-expanding plastic stent is a resilient plastic stent with such expansional strength that a small diameter delivery system may be used to implant the stent, thereby minimizing possible complications for the patient. The stent is made from a braided monofilament, which may be polyetheretherketone (PEEK), polyetherketone (PEK), polyetherketoneketone (PEKK), polyaryletherketone (PAEK), polyetherketoneether-ketoneketone (PEKEKK), or any blends and alloys of these particular resins. The plastic stent may or may not be covered with polymer film. When used, the polymer film includes materials based on polyurethanes, silicones, or materials that biodegrade or erode in the body. Specifically the biodegradable materials might include poly-L-lactide, poly-D-lactide, polyglycolide, ε-caprolactone (epsilon-caprolactone), starch, and collagen or its polymer blends, alloys or copolymers. This material is heat-treated. The monofilament preferably has a diameter of 0.2-0.7 mm. The self-expanding plastic stent demonstrates better mechanical features, processibility, and shape memory.

8 Claims, 1 Drawing Sheet

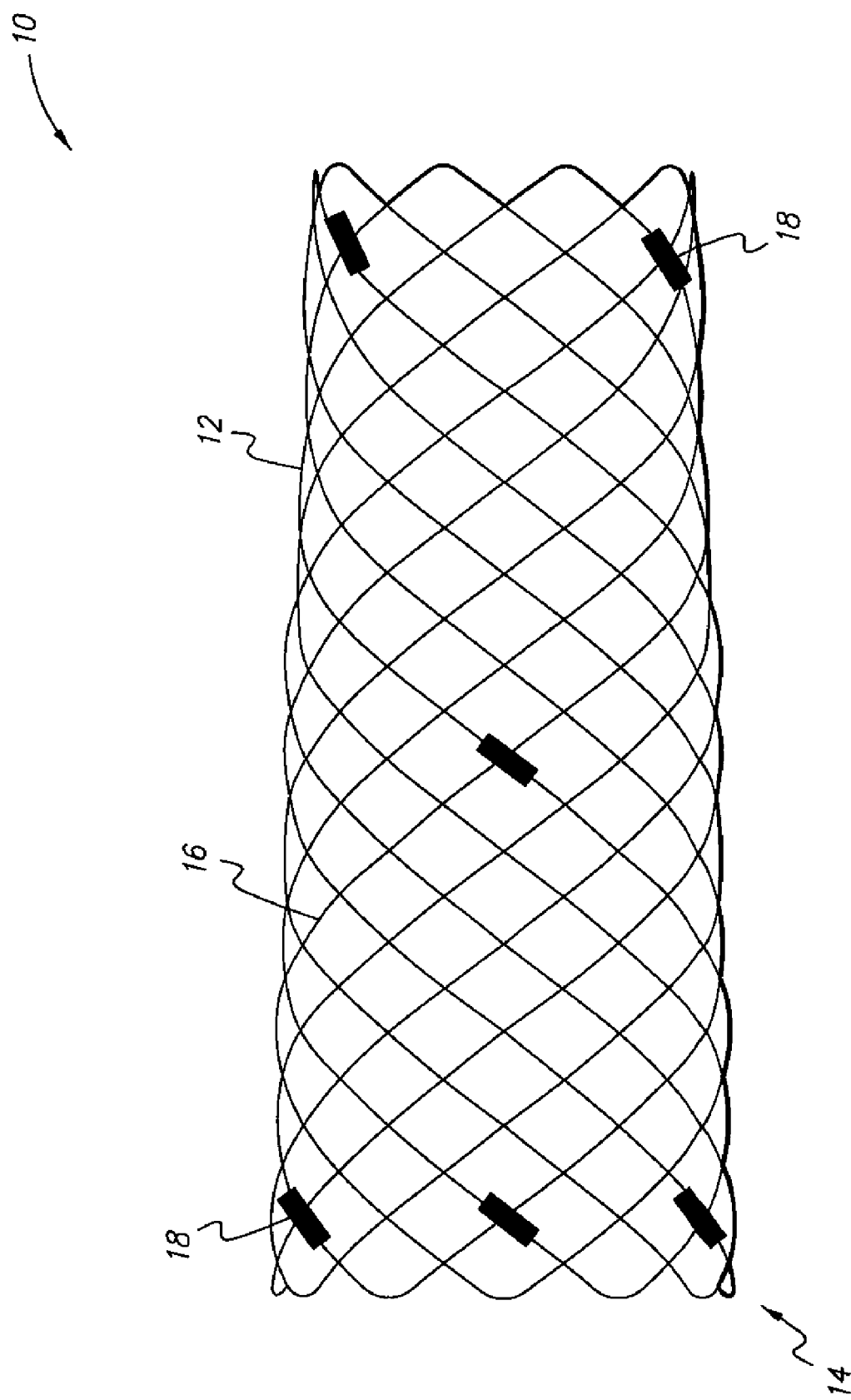

SELF-EXPANDING PLASTIC STENT

CROSS REFERENCE TO RELATED APPLICATIONS

This application claims priority to Czech utility model patent application no. 2009-21803, filed Oct. 12, 2009.

BACKGROUND OF THE INVENTION

1. Field of the Invention

The present invention relates to medical implants, and particularly to self-expandable plastic stents that are compressible for insertion into tubular organs of the body and that expand after insertion to stay in place by resilience of the stents. The stent according to the present invention is to be used predominantly in the esophagus, intestines, biliary ways and air ways.

2. Description of the Related Art

The stents used in the esophagus, intestines, biliary ways and air ways are made both of metal and polymeric materials. When delivering the stent to a desired place, the stent is first compressed into a delivery system, which is then introduced into the respective organ in which the stent is released out of the delivery system in the specified place; the stent spontaneously deploys due to its expansional strength. According to this strength, which can be increased also by the diameter of the used monofilament, it is necessary to choose the appropriate diameter of the delivery system. It is obvious that using the delivery system of a larger diameter is connected with more possible complications for a patient than in cases where there it is possible to use the delivery system of a smaller diameter. Heretofore, known polymeric stents (braided, cut out of tubes etc.) have rather low expansional strength. Thus, they require use of larger diameter delivery systems in order to achieve the appropriate stent expansion after its deployment and to hold the stent in the intended anatomic area.

Thus, a self-expanding plastic stent solving the aforementioned problems is desired.

SUMMARY OF THE INVENTION

The aim of the invention is to create a plastic stent of such expansional strength that the stent allows using a small diameter delivery system, compared to the commonly used self-expandable stents, thereby minimizing possible complications for the patient. The aim is achieved by a stent braided of polyetheretherketone (PEEK) monofilament or polyetherketone (PEK), polyetherketoneketone (PEKK), polyaryletherketone (PAEK), polyetherketoneetherketoneketone (PEKEKK), or any blends and alloys of these particular resins. The plastic stent may or may not be covered with polymer film. The polymer film includes materials based on polyurethanes, silicones, or materials that biodegrade or erode in the body. Specifically, the biodegradable materials may include poly-L-lactide, poly-D-lactide, polyglycolide, ϵ-caprolactone (epsilon-caprolactone), starch, and/or collagen or its polymer blends, alloys or copolymers. This material is heat-treated. Preferably, the monofilament has a diameter of 0.2-0.7 mm. The self-expanding plastic stent has better mechanical features, processibility and shape memory than conventional stents.

These and other features of the present invention will become readily apparent upon further review of the following specification and drawing.

BRIEF DESCRIPTION OF THE DRAWINGS

The sole drawing FIGURE is an elevation view of a self-expanding plastic stent according to the present invention.

DETAILED DESCRIPTION OF THE PREFERRED EMBODIMENTS

The self-expanding plastic stent is a resilient plastic stent with such expansional strength that a small diameter delivery system may be used to implant the stent, thereby minimizing possible complications for the patient. The stent is made from a braided monofilament, which may be polyetheretherketone (PEEK), polyetherketone (PEK), polyetherketoneketone (PEKK), polyaryletherketone (PAEK), polyetherketoneetherketoneketone (PEKEKK), or any blends and alloys of these particular resins. The plastic stent may or may not be covered or coated with polymer film. When used, the polymer film includes materials based on polyurethanes, silicones, or materials that biodegrade or erode in the body. Specifically the biodegradable materials might include poly-L-lactide, poly-D-lactide, polyglycolide, ϵ-caprolactone (epsilon-caprolactone), starch, and collagen or its polymer blends, alloys or copolymers. This material is heat-treated. The monofilament preferably has a diameter of 0.2-0.7 mm. The self-expanding plastic stent demonstrates better mechanical features, processibility, and shape memory.

In the embodiment shown in the sole drawing, the self-expanding plastic stent 10 is made of heat-treated polyetheretherketone (PEEK) monofilament having a diameter of 0.5 mm. This particular stent 10 is designed for placement into the esophagus, although other embodiments of the stent 10 may be designed for implantation into the intestines, the biliary ducts, the airways, or other tubular organs or vessels. In this embodiment, the stent body 12 has a diameter of 16 mm and is radially enlarged into a flare 14 of 25 mm diameter at one end 14. The stent 10 has a length of 60 mm. The monofilaments 16 are braided into cross netting, but the strings may also be made in various shapes and dimensions. The monofilament may be provided with radiopaque markers 18.

It is to be understood that the present invention is not limited to the embodiments described above, but encompasses any and all embodiments within the scope of the following claims.

We claim:

1. A self-expanding plastic esophageal stent, consisting of a heat treated plastic monofilament braided into a tubular body forming an esophageal stent, the tubular body having a length of about 60 mm, a diameter of about 16 mm, and a flared end having a diameter of about 25 mm, the tubular body being resilient, the plastic monofilament has a diameter between 0.2 mm and 0.7 mm, whereby the stent is compressible for insertion by a delivery system into a tubular body structure and expands to prevent constriction of the tubular body structure after implantation, wherein the plastic monofilament comprises:

a monofilament made from at least one resin selected from the group consisting of polyetheretherketone (PEEK), polyetherketone (PEK), polyetherketoneketone (PEKK), polyaryletherketone (PAEK), polyetherketoneether-ketoneketone (PEKEKK); and a polymer film at least partially covering the monofilament, the polymer film being a biodegradable polymer.

2. The self-expanding plastic stent according to claim 1, wherein the plastic monofilament consists of a polyetheretherketone (PEEK) monofilament.

3. The self-expanding plastic stent according to claim 1, wherein the plastic monofilament consists of a polyetherketone (PEK) monofilament.

4. The self-expanding plastic stent according to claim 1, wherein the plastic monofilament consists of a polyetherketoneketone (PEKK) monofilament.

5. The self-expanding plastic stent according to claim 1, wherein the plastic monofilament consists of a polyaryletherketone (PAEK) monofilament.

6. The self-expanding plastic stent according to claim 1, wherein the plastic monofilament consists of a polyetherketoneetherketoneketone (PEKEKK) monofilament.

7. The self-expanding plastic stent according to claim 1, wherein the biodegradable polymer is at least one polymer selected from the group consisting of poly-L-lactide, poly-D-lactide, polyglycolide, $\epsilon$-caprolactone (epsilon-caprolactone), starch, and collagen.

8. The self-expanding plastic stent according to claim 7, wherein the biodegradable polymer is a copolymer made from at least two polymers selected from the group consisting of poly-L-lactide, poly-D-lactide, polyglycolide, $\epsilon$-caprolactone (epsilon-caprolactone), starch, and collagen.

* * * * *